US010189934B2

(12) United States Patent
Piletsky et al.

(10) Patent No.: US 10,189,934 B2
(45) Date of Patent: Jan. 29, 2019

(54) PREPARATION OF MOLECULARLY IMPRINTED POLYMERS (75) Inventors: Sergey Anatollyovich Piletsky, Cranfield (GB); Antonio Ricardo Leonardo Guerreiro, Cranfield (GB); Michael James Whitcombe, Easton (GB)

(73) Assignee: MIP DIAGNOSTICS LIMITED, Leicester (GB)

( * ) Notice: Subject to any disclaimer, the term of this patent is extended or adjusted under 35 U.S.C. 154(b) by 1174 days.

(21) Appl. No.: 13/512,618

(22) PCT Filed: Dec. 1, 2010

(86) PCT No.: PCT/GB2010/002213
§ 371 (c)(1),
(2), (4) Date: Jun. 15, 2012

(87) PCT Pub. No.: WO2011/067563
PCT Pub. Date: Jun. 9, 2011

(65) Prior Publication Data
US 2012/0270964 A1  Oct. 25, 2012

(30) Foreign Application Priority Data
Dec. 1, 2009  (GB) .................................. 0921025.3

(51) Int. Cl.
| *C08F 293/00* | (2006.01) |
| *B01J 20/26*  | (2006.01) |
| *C08F 220/28* | (2006.01) |
| *C08F 2/46*   | (2006.01) |
| *C08F 2/48*   | (2006.01) |

(52) U.S. Cl.
CPC ......... *C08F 293/005* (2013.01); *B01J 20/268* (2013.01); *C08F 2438/03* (2013.01); *G01N 2600/00* (2013.01)

(58) Field of Classification Search
CPC .. C08F 2/46; C08F 2/48; C08F 220/28; C08F 293/00
USPC ..................................................... 526/317.1
See application file for complete search history.

(56) References Cited

U.S. PATENT DOCUMENTS

| 5,630,978 | A  |   | 5/1997  | Domb |
| 6,127,154 | A  | * | 10/2000 | Mosbach ................ B82Y 5/00 |
|           |    |   |         | 210/660 |
| 6,458,599 | B1 |   | 10/2002 | Huang |
| 6,852,818 | B1 |   | 2/2005  | Piletshy et al. |
| 7,288,415 | B2 |   | 10/2007 | Huang |
| 7,393,909 | B2 |   | 7/2008  | Sellergren et al. |
| 2002/0198349 | A1 | * | 12/2002 | Norton ........................ 526/319 |
| 2004/0157209 | A1 | * | 8/2004  | Yilmaz et al. .................... 435/5 |
| 2008/0311072 | A1 | * | 12/2008 | Karim et al. ............... 424/78.36 |
| 2014/0228472 | A1 | * | 8/2014  | Piletsky et al. ............... 522/174 |

FOREIGN PATENT DOCUMENTS

WO      WO 96/40822         12/1996

OTHER PUBLICATIONS

Wulff, G. Makromol. Chem. Macromol. Symp., 1993, 70/71, 285.
Vlatakis, G.; et al. Nature, 1993, 361, 645.
Moad, G.; Rizzardo E.; Solomon, D.H. Macromolecules 1982, 15, 909.
Matyjaszewski, K.; Xia, J. Chem. Rev. 2001, 101, 2921.
Kamigaito, M.; Ando, T.; Sawamoto, M. Chem. Rev. 2001, 101, 3689.
Hawker, C. J.; Bosman, A. W.; Harth, E. Chem. Rev. 2001, 101, 3661.
Fischer, H. Chem. Rev. 2001, 101, 3581.
Otsu, T.; Matsumoto, A. Adv. Polym. Sci. 1998, 136, 75-137.
Moad, G.; et al. Polym. Int. 2000, 49, 993-1001.
Ruckert, B.; Hall, A. J.; Sellergren B. J. Mater. Chem. 2002, 12, 2275.
Hattori, K.; et al. J. Membr. Sci. 2004, 233, 169.
Li,Z.; Day, M.; Ding, J. F.; Faid, K. Macromolecules. 2005, 38, 2620.
Guerreiro A. R., Chianella I., Piletska E., Whitcombe M. J., Piletsky S. A. (2009). Biosens. Bioelectron., 24, 2740-2743.
Jagur-Grodzinski, J. Reactive & Functional Polymers. 2001, 49, 1.
Shim, S.E. et al. Macromolecules. 2003, 36, 7994-8000.
Yu, Q.; Zeng, F.; Zhu S. Macromolecules. 2001, 34, 1612.

* cited by examiner

Primary Examiner — Fred M Teskin
(74) Attorney, Agent, or Firm — Chace Ruttenberg & Freedman, LLP (57) ABSTRACT A polymerization process, preferably a living radical polymerisation process, is carried out in the presence of a template substance, to produce molecularly imprinted polymers ("MIPs"). It is controlled so that the products are quite small (500-$10^6$ Daltons) so that they are soluble or form colloidal suspensions. The template substances are immobilized templates, which can be re-used. Immobilized templates are also useful for purification of MIP solutions/suspensions by affinity chromatography.

12 Claims, 2 Drawing Sheets

PREPARATION OF MOLECULARLY IMPRINTED POLYMERS

FIELD OF THE INVENTION

The invention relates to the field of organic synthesis and polymer chemistry, and particularly to the area concerned with the methodology for the preparation of organic molecules by template-directed synthesis and template polymerization.

BACKGROUND OF THE INVENTION

The term "template-directed synthesis" includes the formation of a new substance by chemical modification of a substrate, or by the coupling of two or more molecules in the presence of a template that serves as a pattern for new structure formation. The most well known example of this process is gene transcription. A particular example of template-directed synthesis is template polymerization, where the formation of a polymeric receptor (replica) proceeds in the presence of another polymer or small molecular weight organic substance (the template). Prior to the initiation of polymerization, and during polymerization, the monomers spatially distribute themselves (self-assembly process) around the template molecules in accordance with the size, polarity and functionality of the template. The monomers are polymerised either into linear chains or rigid three-dimensional networks. A specific example of template polymerization is molecular imprinting, based on the polymerization of vinyl or acrylic monomers in the presence of template (see ref. 1, 2). The traditional approach involves the production of highly cross-linked imprinted polymers, which are insoluble in aqueous and organic solvents. Because of their inherent insolubility, the possibility to use molecularly imprinted polymers (MIPs) in pharmacology and medicine is restricted.

Recently, several attempts have been made to develop protocols for the preparation of imprinted polymers with relatively low-molecular weights, which could exist in soluble or at least colloidal forms. This format will allow polymers to be used as biologically active molecules (drugs, effectors, modulators, inhibitors) in pharmacology and medicine, as "plastic antibodies", replacing biological molecules in sensors and in affinity separation and as catalysts with enzyme-like properties.

In one such example, MIP molecules were synthesized by polycondensation of amino acids and nucleotides around a biological receptor, enzyme, nucleic acid, cell, virus, micro organism, tissue sample or drug (see U.S. Pat. No. 6,852, 818). In another example, different methods were used to produce oligomeric and polymeric MIPs (see U.S. Pat. No. 6,127,154). Most of the examples in the prior art describe the preparation of high-molecular weight cross-linked polymers, which require hydrolysis in order to deliver soluble or colloidal particles stable in solution. In one such example, (see U.S. Pat. No. 6,127,154) researchers used specially designed compounds containing photoactive perfluorophenylazido groups capable of coupling upon illumination. In this case, affinity ligands could be synthesized as soluble particles. In all of these cases, the synthesized compounds were composed of a number of fractions with poorly controlled size and properties. Other approaches for the synthesis of molecules with biological activity are described in PCT Patent Publication WO 96/40822 and in U.S. Pat. No. 5,630,978, where chemical compounds were prepared in the presence of a template-imprinted polymer, which in turn was prepared in the presence of another template, normally a drug such as heparin. The resulting replica is a ligand molecule, which has no affinity to the template and rather resembles the structure of the original drug molecule itself.

One of the ways to produce nanoparticles is through the use of controlled condensation or additive radical "living" polymerization. The living free-radical polymerization techniques, such as iniferter polymerization, nitroxide-mediated radical polymerization, atom-transfer radical polymerization (ATRP) and reversible addition-fragmentation chain-transfer (RAFT) polymerization, open new routes for the synthesis of polymers with relatively controlled low-molecular weights (see ref. 3-9). Controlled/living polymerization techniques are based on a delicate balance between dormant and active species that effectively reduces the concentration of propagating entities in the system and minimizes the extent of termination. Living polymerization could be free of side reactions such as termination and chain transfer and thus can generate polymers with well-defined molecular weight distributions and structures. The same approach can be applied to the formation of copolymers, thus making it possible to produce block copolymers by free radical polymerization by proper sequencing of the monomer additions. Living polymerization has been used previously in the production of bulk grafted MIPs (see ref. 10, 11). Soluble polymers were also produced by living polymerization and used later in MIP production (see ref. 12). Recently, controlled living polymerization was used for the preparation of MIP nanoparticles (13).

One of the complications in MIP synthesis is the frequent need to use templates, which are expensive and/or difficult to obtain, such as proteins, some toxins etc. that are difficult to recover after polymerization and limit the amount of MIP that can be obtained. Ideally the template should be capable of being recycled to overcome these limitations. The optimal way to achieve this is by using the template in an immobilized form. Immobilized template has been used previously (see U.S. Pat. No. 7,393,909). In that case, the template was immobilized onto a silica surface and polymer was formed in pores around it. By dissolving the silica support and removal of the template, MIPs of various morphologies were obtained. In all of the examples disclosed in U.S. Pat. No. 7,393,909, the surface bearing the immobilized template is lost during the dissolution process and cannot be recycled. In other examples, immobilized templates were used for the production of imprinted surfaces (see U.S. Pat. Nos. 6,127, 154; 6,458,599; and 7,288,415). Potentially the template-bearing surfaces disclosed in these reports can be regenerated and used several more times. These approaches can be used for the production of sensors or arrays, but would be difficult to adapt for the production of nanoparticles or small soluble molecules.

Yet another major problem associated with MIPs is the heterogeneity of the binding sites produced, which is generally responsible for high levels of non-specific binding. This problem has been rectified by affinity separation of separately produced MIP nanoparticles on a column with immobilized template (13). It is clear that in order for affinity separation to be possible, MIPs should be in a suitable form, preferably in the form of nanoparticles.

The current invention addresses all of these problems relating to the development of high performance cross-linked MIP nanoparticles by proposing a combination of two techniques: (i) performing controlled polymerization, optionally controlled radical polymerization, in the presence of a surface or surfaces bearing immobilized template to form imprinted nanoparticles and (ii) retaining the nanoparticles by affinity interaction with immobilized template for selection and purification purposes.

Background material can be found in the following references:
1. Wulff, G. *Makromol. Chem. Macromol. Symp.*, 1993, 70/71, 285.
2. Vlatakis, G.; et al. *Nature*, 1993, 361, 645.
3. Moad, G.; Rizzardo E.; Solomon, D. H. *Macromolecules* 1982, 15, 909;
4. Matyjaszewski, K.; Xia, *J. Chem. Rev.* 2001, 101, 2921.
5. Kamigaito, M.; Ando, T.; Sawamoto, M. *Chem. Rev.* 2001, 101, 3689.
6. Hawker, C. J.; Bosman, A. W.; Harth, E. *Chem. Rev.* 2001, 101, 3661.
7. Fischer, H. *Chem. Rev.* 2001, 101, 3581.
8. Otsu, T.; Matsumoto, A. *Adv. Polym. Sci.* 1998, 136, 75-137.
9. Moad, G.; et al. *Polym. Int.* 2000, 49, 993-1001.
10. Ruckert, B.; Hall, A. J.; Sellergren B. *J. Mater. Sci.* 2002, 12, 2275.
11. Hattori, K.; et al. *J. Membr. Sci.* 2004, 233, 169.
12. Li, Z.; Day, M.; Ding, J. F.; Faid, K. *Macromolecules*. 2005, 38, 2620.
13. Guerreiro A. R., Chianella I., Piletska E., Whitcombe M. J., Piletsky S. A. (2009). *Biosens. Bioelectron.*, 24, 2740-2743.
14. Jagur-Grodzinski, J. *Reactive & Functional Polymers.* 2001, 1, 1.
15. Shim, S. E. et al. *Macromolecules*. 2003, 36, 7994-8000.
16. Yu, Q.; Zeng, F.; Zhu S. *Macromolecules.* 2005, 34, 1612.
17. U.S. Pat. No. 7,019,072—Method of preparing latex for coating paper, 2006.

Additional patent references include:
1. U.S. Pat. No. 6,852,818 issued 8 Feb. 2005 entitled MOLECULARLY IMPRINTED POLYMERS PRODUCED BY TEMPLATE POLYMERIZATION.
2. U.S. Pat. No. 6,127,154 issued 3 Oct. 2000 entitled METHODS FOR DIRECT SYNTHESIS OF COMPOUNDS HAVING COMPLEMENTARY STRUCTURE TO A DESIRED MOLECULAR ENTITY AND USE THEREOF.
3. PCT Patent Publication WO96/40822 entitled PREPARATION OF BIOLOGICALLY ACTIVE MOLECULES BY MOLECULAR IMPRINTING.
4. U.S. Pat. No. 5,630,978 issued 20 May 1997 entitled PREPARATION OF BIOLOGICALLY ACTIVE MOLECULES BY MOLECULAR IMPRINTING.
5. U.S. Pat. No. 7,393,909 issued 1 Jul. 2008 entitled POROUS, MOLECULARLY IMPRINTED POLYMER AND A PROCESS FOR THE PREPARATION THEREOF.
6. U.S. Pat. No. 6,458,599 issued 1 Oct. 2002 entitled COMPOSITIONS AND METHODS FOR CAPTURING ISOLATING DETECTING ANALYZING AND QUANTIFYING MACROMOLECULES.
7. U.S. Pat. No. 7,288,415 issued 30 Oct. 2007 entitled COMPOSITIONS AND METHODS FOR CAPTURING ISOLATING DETECTING ANALYZING AND QUANTIFYING MACROMOLECULES.

SUMMARY OF THE INVENTION

According to the invention there is provided a process for the preparation of a molecularly imprinted polymer ("MIP") in the form of a solution or colloidal suspension of MIP particles, comprising the steps of: (a) providing a carrier substance having a template material immobilized on it so as to be exposed at a surface; (b) providing a polymerizable composition in contact with said surface; (c) effecting controlled polymerization of said polymerizable composition in contact with said surface, said polymerization being terminated when MIP particles capable of forming solution or colloidal suspension have been formed; and (d) separating said MIP particles from said surface. A colloidal suspension is desirably stable. It desirably consists of fine particles, under 1 micrometer. The invention involves the application of controlled polymerization, optionally controlled radical polymerization, performed in the presence of immobilized (convex) template for producing soluble or colloidal cross-linked MIP particles.

Preferred embodiments of the invention may provide one or more of the following benefits:
1. MIP nanoparticles can be synthesized using automatic protocol (i.e., by machine).
2. Synthesized MIPs do not contain template, which remains bound to the solid surface.
3. It is possible to use ANY solvent during MIP preparation.
4. The process of MIP synthesis, separation and purification is very fast (minutes to a few hours).
5. The template is not wasted and process of MIP synthesis can be repeated several times, which reduces the cost of MIP preparation for expensive templates.
6. There is the possibility to add extra steps when synthesized particles still on the immobilized template are further functionalized, e.g. by adding fluorescent label, or a non-adhesive coating.
7. There is the possibility to control size of synthesized particles.
8. There is the possibility to fractionate synthesized nanoparticles and to collect fractions with different affinities.

In the method described here, the MIPs are produced in the presence of an immobilized template using controlled polymerization, optionally controlled radical polymerization, techniques. Various techniques useful for producing nanoparticles by controlled polymerization are known to specialists familiar with the art. The polymerization reaction is terminated at a stage when the size of the synthesized molecules is relatively small. The product of such a process could exist either in soluble or stable colloidal form in solution or suspension. The colloidal suspensions or solutions of MIPs according to this invention may be in either aqueous or organic liquids.

The synthesized molecules have a structure complementary to that of the original template and have the ability to bind it with reasonably high affinity. For the purpose of clarification, in the present invention "high affinity" and "high performance" MIPs are defined as these polymers with affinity exceeding affinity of typical corresponding "Blank" polymers by at least three, preferably at least five, times. Here, the designation "Blank" polymer refers to the product of the polymerization process used to form the MIP carried out in the absence of template. These synthetic molecules (polymers and oligomers) have predetermined affinities and specificities, superior activity to randomly synthesized polymers and can be prepared much more easily than specifically designed discrete organic structures. The polymerization process to form MIPs, as described herein, might be imperfect and result in the formation of both high and low-affinity particles (formed e.g. in solution where template is not present). The high affinity particles can be selectively bound (and later recovered) to surfaces with immobilized template, allowing them to be separated from low affinity particles. The surfaces with immobilized template can be the same surfaces which are used in the formation of the MIPs or they can be separate surfaces (e.g. contained within a separate column) with immobilized template. The surfaces mentioned here can be surfaces of affinity columns, sensor devices, microfluidic devices, microchips, reactors, beads, fibres, wells, microplates, membranes, filters, pits, nanostructures, vesicles, capsules etc. The surface can be solid, semi-solid or liquid or fluid (as in the case of micelles or interfaces). Optionally the particles can be further screened using an additional column or columns, to select a subfraction of the particles that do not possess affinity for a potential interferent compound. A similar approach can be employed to select subfraction(s) of particles that additionally have affinity to one or more analogues of the template in order to produce "class-selective" binders.

Molecules synthesized as described in this invention (dimers, oligomers, polymers, or their mixture) can be used as drugs in pharmacology and medicine, as receptor-specific ligands in analytical chemistry (sensors, assays), for separation in the biotechnology, pharmaceutical and food industries and as catalysts in synthesis or as replacements for enzymes in assays, sensors and other applications such as washing powders. Previous efforts in drug design have typically been based upon the cumbersome investigation of structure-activity relationships of large numbers of chemical structures. The present invention describes a simpler and more direct method—controlled polymerization, optionally controlled radical polymerization, for the formation of cross-linked MIP nanoparticles in the presence of immobilized template to design a biologically-active substance, which should be of great benefit (in comparison with traditional drug design and discovery methods) as well as useful ligands for affinity separation, sensors and catalysis. Important aspects of the invention include:

(1) Synthesis of the cross-linked MIP nanoparticles by controlled polymerization, optionally controlled radical polymerization, in the presence of an immobilized template which can be a biological receptor, nucleic acid, cell, spore, virus, microorganism, tissue sample, carbohydrate, oligosaccharide, polysaccharide, peptide, nucleoprotein, mucoprotein, lipoprotein, synthetic protein, glycoprotein, glucosaminoglycan, steroid, immunosuppressant, hormone, heparin, antibiotic, vitamin, biomarker of a pathological or disease state, toxin, pesticide, herbicide, explosive, nerve agent, pollutant, endocrine disrupting compound, nucleotide, nucleoside, oligonucleotide, metabolite, secondary metabolite, drug metabolite, drug intermediate or drug. This list is not intended to be limiting but representative of some potential classes of template, the full extent of which will be understood by those skilled in the art.

(2) Optimization of the conditions of the reaction in order to generate particles with relatively small size.

(3) Synthesis of the molecules, including biologically-active molecules, from functional monomers, which can include one or more of: vinyl monomers, allyl monomers, acetylenes, acrylates, methacrylates, acrylamides, methacrylamides, chloroacrylates, itaconates, trifluoromethylacrylates, derivatives of amino acids, nucleosides, nucleotides, and carbohydrates.

(4) Retaining the synthesized high-affinity particles by affinity interactions taking place on the same surface with immobilized template used for MIP preparation or on different surfaces, also containing immobilized template or a template analogue.

(5) Sequential polymerization when imprinted polymer particles retained on the surface with immobilized template are modified with other types of molecules in order to change the properties or functions of the synthesized molecules.

(6) The application of the synthesized molecules as drugs in pharmacology and medicine, as receptor-specific ligands in analytical chemistry (sensors, assays), for separation in biotechnology, pharmacology and food industry or as catalysts.

DETAILED DESCRIPTION

The polymers prepared as described in the invention resemble effectors (activators, inhibitors or substrates) of the template, and as such can have biological activity if the template is involved in a physiological process or an effective analogue of such a molecule or structure. Such polymers can be used, for example, as drugs in pharmacology and medicine. The benefits coming from this approach are numerous, including the possibility to reuse immobilized template for MIP synthesis, the possibility to fractionate MIPs with high affinity from low affinity particles and unreacted monomers, easy removal of the synthesized MIPs from the template, the ability to post-functionalise MIPs attached to immobilized template, the ability to fully or partially automate the manufacturing process etc. Other benefits of the invention should be evident to those skilled in the art.

Specifically, in one aspect, the invention relates to the synthesis of cross-linked MIPs by controlled polymerization, optionally controlled living radical polymerization (LRP); or living anionic polymerization; living cationic polymerization; and controlled polycondensation in the presence of an immobilized template which can be a biological receptor, nucleic acid, cell, spore, virus, microorganism, tissue sample, carbohydrate, oligosaccharide, polysaccharide, peptide, nucleoprotein, mucoprotein, lipoprotein, synthetic protein, glycoprotein, glucosaminoglycan, steroid, hormone, immunosuppressant, heparin, antibiotic, vitamin, biomarker of a pathological or disease state, toxin, pesticide, herbicide, explosive, nerve agent, pollutant, endocrine disrupting compound, nucleotide, nucleoside, oligonucleotide, metabolite, secondary metabolite, drug metabolite, drug intermediate or drug or other class of template known to those skilled in the art. The template can be immobilized onto polymeric, polysaccharide or glass surfaces, for example in the form of beads, a waveguide, fibres, membranes, or capillaries or any other surface suitable for an intended application, as known to those skilled in the art.

Polymerization can be initiated for example by heating, by applying current (electropolymerization), by the addition of redox catalyst(s), persulfate or peroxides, by irradiation, including gamma radiation or by microwave radiation or preferably by irradiation with UV or visible light and normally takes minutes or hours depending on the reactivity of the species.

Several different forms of controlled polymerization are covered by the current invention. They all are based on the ability to control the addition or condensation reaction at a level such that predominantly soluble nanoparticles are formed rather than continuous polymer layers or networks. In the example of living radical polymerization initiator molecules undertake reversible transformations by thermal, chemical, or photochemical stimuli, reversibly transforming dormant species into reactive free radicals or ions, which act as chain propagators. For this condition to apply, the equilibrium constants of the reactions should favor formation of the dormant species and should allow rapid exchange between the dormant and propagating species. Thus the concentrations of the propagating species will be very low and their residence time very short, which reduces the probability of side reactions that lead to termination of the growing polymer chain. Some examples of living polymerization include, but by all means are not limited to: nitroxide-mediated polymerization (NMP), atom-transfer radical polymerization (ATRP) and reversible addition-fragmentation chain-transfer polymerization (RAFT). The RAFT polymerization is based on reversible addition-fragmentation chain transfer equilibrium, where there is an exchange between active and dormant species. The radicals generated in the initiation step will propagate by addition of monomer until a molecule, capable of acting as a chain transfer agent, is encountered, and to which they may add in a reversible fashion. Generally, the living polymerization process allows for the use of iniferters (initiator transfer-agent terminator), which optionally can be made in conjunction with conventional initiators to confer a living nature to the polymerization. Iniferters can be photo-iniferters bearing a dithiocarbamyl group or thermal-iniferters carrying carbon-carbon or azo groups (see e.g., ref. 14) or other types of compound known to those skilled in the art. The preferred kind of iniferters are those that yield different radicals, one carbon radical which is reactive and another one less reactive radical, e.g., a dithiocarbamyl radical. The carbon radical, which is typically a benzyl radical, can react with unsaturated monomer to initiate polymerization. The less reactive radical, for example a dithiocarbamyl radical, can terminate the polymerization by recombining with a growing polymer chain, however the product of termination can be further dissociated to a new propagating radical and terminator in response to continued application of the stimulus, e.g. UV irradiation (see e.g., ref. 15).

Other compounds which could be used as initiators for different types of living polymerization (atom transfer, anionic, cationic etc.) covered by the scope of invention include but are not limited to: 2-bromopropionitrile with Cu(I)Br complexed with N,N,N',N'',N''-pentamethyldiethylenetriamine, polystyrene bromo macroinitiator with Cu(I) Cl/PMDETA; ethyl 2-bromoisobutyrate with CuCl/bipyridine; 1,4-bis(2,6-diisopropylphenyl) acenaphatenediiminenickel (II) dibromide; 2,2-dimethoxy-2-phenyl acephenone in combination with tetraethylthiuram disulfide; tetraphenyl biphosphine; tertiary peroxides such as di-tert-butyl peroxide; $SmMe(C_5Me_5)_2(THF)$; styrene-based epoxides in conjunction with $TiCl_4$; methylstyrene tetramer disodium; $MoOCl_4$-n-BuSn-EtOH; $HCl/ZnCl_2$; methyl p-toluenesulphonate; 2,10,15,20-tetraphenylporphinato aluminium methyl; 3-methyl-1,1-diphenylpentyllithium; butyllithium in THF; molybdenum alkylidine compounds; bifunctional organolanthanide(III); Mo(CH-t-Bu)(NAr)(OCMe$_3$)$_2$ and Mo(CHCPhMe$_2$)(NAr)(OCMe(CF$_3$)$_2$)$_2$; HI/I$_2$; Zr, Ti and Hf complexes combined with either methylaluminoxane or phenyl borates; diimide complexes of Pd, Ni, Fe or Co; homogeneous Ta, Ti, Mo, W carbene complexes; rare earth metal complexes composed of metallocene type or non-metallocene type complexes; cationic monocyclopentadienyl zirconium acetamidinate complexes; esterified fluorinated telomers with one or two hydroxyl group as initiators for copper mediated living polymerization; Yb[C(SiMe$_3$)$_3$]$_2$.

One advantage of living polymerization in contrast to traditional radical polymerization is that the former proceeds at a low rate and with no observable autoacceleration, while the latter frequently proceeds with a strong autoacceleration (see e.g., ref. 16). The invention takes advantage of this by performing living polymerization under conditions that favor the formation of polymers with relatively low molecular weight. Typically the reaction is stopped at an early stage to produce polymers with molecular weights of between 500 and 1,000,000 Da.

Use may be made of optimization of the conditions of the reaction in order to generate particles with relatively small size. An important part of the process is the selection of an appropriate living initiator and optimization of the conditions of the polymerization reaction. Alternatively the rate of radical formation and propagation can be controlled by adding inhibitors of the reaction or chain transfer agents such as mercapto derivatives (17).

Living radical polymerization initiators can be prepared from discrete organic molecules or from macromolecules. Most compounds that contain a hydroxyl, carboxylic or amino groups can be converted into an initiator, and thus incorporated easily into the polymer. This can either be at the terminus of the polymer in the case of a mono-functional initiator, or in the middle of the polymer in the case of a multi-functional initiator.

The reaction conditions favoring formation of relatively low molecular weight polymers include, but are not limited to: (i) using stoichiometric ratio between initiator and monomers; (ii) cooling the reaction or removing the source of UV or other irradiation, which will terminate the formation of new propagating species at an early stage of the reaction; (iii) removal of the monomers from contact with the growing polymer chain e.g., by filtration or chromatography; (iv) adding inhibitors to the reaction; (v) performing polymerization in very dilute solution; (vi) adding chain transfer agents. The preferable option would be removal of the source of irradiation or its interruption. Alternatively monomers and other reagents can be removed from the growing MIP attached to the immobilized template by elution. As a result of controlled living polymerization, MIP particles can be formed in the size range 500-1,000,000 Da, and can exist in soluble form or as larger particles (but under 1 micrometer), which can exist in the form of fine colloids that are stable in solution and compatible with the conditions of affinity chromatography.

Monomers that can be used for MIP preparation, include: vinyl monomers, allyl monomers, acetylenes, acrylates, methacrylates, acrylamides, methacrylamides, chloroacrylates, itaconates, trifluoromethylacrylates, derivatives of amino acids (e.g. esters or amides), nucleosides, nucleotides, and carbohydrates. In other aspect of the proposed invention polymerization is performed in the presence or on the surface of particles containing double bonds. Cross-linking monomers are used to fix or stabilise the structure of the resulting replica molecule, so that it remains complementary to that of the template. Typical examples of cross-linkers suitable for MIPs include, but are not limited to, ethylene glycol dimethacrylate, trimethylolpropane trimethacrylate, divinylbenzene, methylene bisacrylamide, ethylene bisacrylamide and N,N'-bisacryloylpiperazine. The function of cross-linking agents can be performed by particles or precursor polymers containing double bonds, or particles or polymers with multiple functionalities attached which can bind to functional monomers. Those skilled in the art can select monomers and cross-linkers suitable for a particular system. Alternatively a variety of combinatorial and computational methods can be used to assist in this selection.

The synthesized nanoparticles have higher affinity to the immobilized template than monomers, non-specific oligomers and low affinity polymers (e.g. those formed in the bulk volume in the absence of template). Thus, in one aspect of the invention, weakly bound material is removed from the nanoparticles attached to the immobilized template by washing. The separation of high-affinity nanoparticles from immobilized template is achieved by heating, which disrupts complex formation by changing solution pH, changing ionic strength, or through the addition of urea, guanidine, or a substance that interacts with the template more strongly than does the MIP.

The synthesized affinity MIP nanoparticles may be purified additionally by chromatography, filtration and/or electrophoresis. The separation of the synthesized polymer can be achieved by affinity chromatography, or selective elution, when the same or similar immobilized template is used for the purification of polymer fraction with the highest affinity to the template, or/and by gel permeation chromatography, which separates polymer fractions with different size. The fractionation, separation and purification may be achieved using buffers with different pH, ionic strength, or through the addition of urea, guanidine, or substances which interact with the template more strongly than does the polymer. Alternatively fractionation of particles with high affinity can be achieved by filtration, electrophoresis, chromatographic separation, washing, centrifugation or dialysis. Affinity chromatography is a particular powerful tool, and is particularly preferred, because it allows for the preparation of MIPs with a narrow distribution of affinities to the template.

Growing polymer chains can be modified with another polymer or functional group with the intention of introducing a specific property to the MIPs which would facilitate its extraction or other form of separation. An example of this is a polymer with a hydrophobic tail, which would allow for example extraction of the polymer from aqueous solution by organic solvent. It would be possible to introduce a specific binding group, e.g., biotin, which would allow selective removal of the polymer by affinity adsorbent. Those skilled in the art will be familiar with the wealth of experimental protocols that allow this modification and corresponding separation to be performed. The modification can be achieved directly on the surface while the polymer is bound to immobilized template or separately.

The invention may employ sequential polymerization, when the imprinted polymer is modified with other types of molecules in order to change the properties or functions of the synthesized molecules. It has been mentioned already that the growing polymer chain can be modified with another polymer or functional group to facilitate its separation. One important property of living polymerization is the ability to stop a reaction and continue it later by simply stopping e.g., UV irradiation of the reaction mixture. The end of the growing polymer chain contains initiator, which can be activated again to initiate a new round of polymerization. Thus the growing polymer chain can be exposed to another monomer and the polymerization continued, resulting in the formation of block copolymers. The new monomer can introduce a new functionality into the polymer.

Thus in addition to the affinity to the first template, provided by the first MIP, an extended polymer can be produced with affinity to a second template introduced into the system. The extended block polymer could have fluorescent tags attached to end groups, which would be useful in diagnostics. Other types of modification are also possible, to introduce other functionalities such as the ability to generate active species with biocidal properties, catalytic groups, isotopic labels, groups useful for immobilisation, sensing and imaging (e.g. contrast agents) etc. These functionalities could also be introduced into the polymer by using the correspondingly functionalised initiator. The modification can be achieved directly on the surface while the particle is bound to immobilized template or separately.

In one aspect, the invention relates to applications of the synthesized molecules as drugs in pharmacology and medicine, as receptor-specific ligands in analytical chemistry (sensors, assays), for separations in biotechnology, pharmacology and food industry and as catalysts. The soluble nature of the synthesized polymers makes them ideal candidates for use as drugs. The selective binding to an enzyme, receptor or other biological molecule could be used to affect biological functions of these molecules. Thus MIPs synthesized by living polymerization could be used in vivo for modulation of biological processes. When bound with isotopes or fluorescent tags MIPs could be used as selective contrast agents or in other forms of diagnostics. MIPs integrated with ligands capable of producing in certain conditions e.g., singlet molecular oxygen, could be used as selective biocidal agents. A variety of other modifications could be proposed by those skilled in the art to introduce antibiotic properties into MIPs prepared by living polymerization.

The synthesized MIPs can be used as substitutes for natural antibodies or receptors in different forms of assays and sensors. Several features make MIPs prepared by living polymerization particularly attractive objects for the application in sensors. Thus synthesized MIP molecules still contain initiator, which can be used to covalently attach polymers to the solid surfaces. Thus simple UV irradiation might be sufficient to bind MIPs to surfaces covered with double bonds.

The ability to use affinity chromatography to separate MIP ligands into several fractions with different affinities can be advantageous for the preparation of sensors/assays with varying detection ranges. For some applications Blank polymers prepared by living polymerization in the absence of template could also be used. It would be necessary however to prepare such polymers using monomers which possess certain affinity or other properties necessary for this particular application. Those skilled in the art know how to select such monomers by using e.g. computational or combinatorial approaches. It is necessary to clarify that using both MIPs and Blank polymers prepared in a fashion as described in the corresponding embodiments are covered by the scope of the present invention.

The invention will now be further described particularly with references to the following non-limiting examples.

EXAMPLES

Example 1

Synthesis of MIP Particles with Affinity to Melamine

Figure 3:
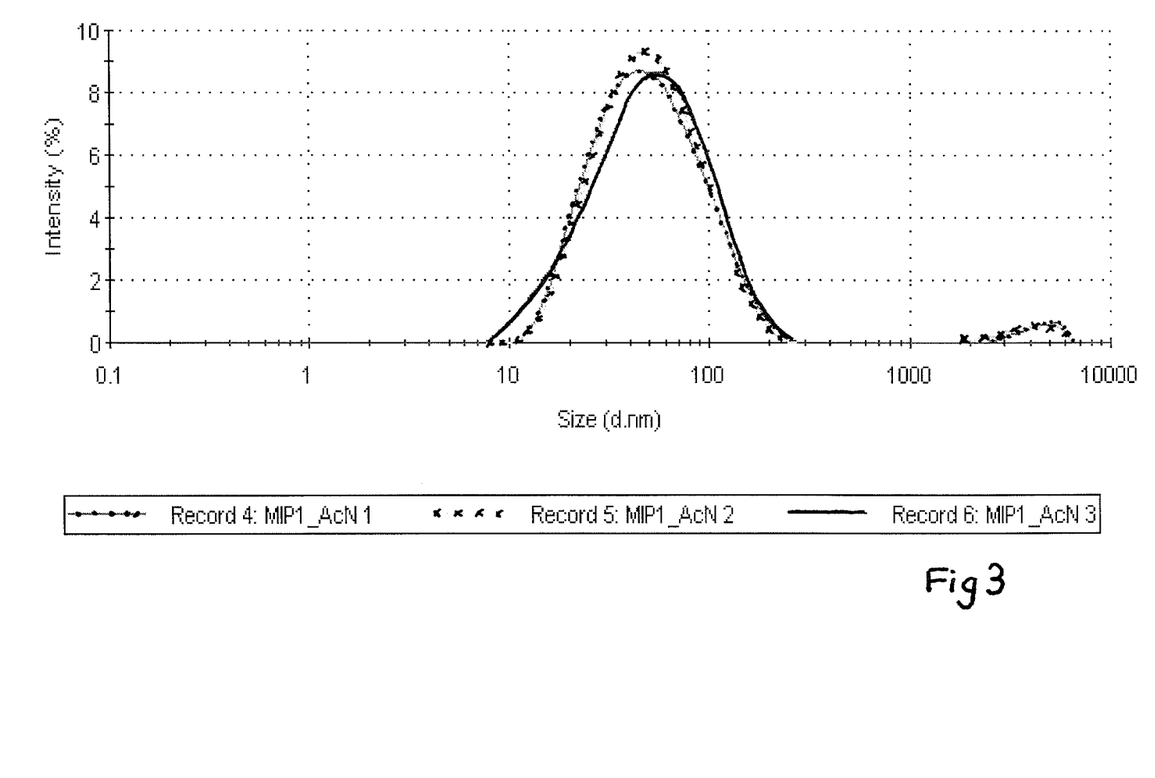
FIG. 3 depicts the size distribution of MIP nanoparticles imprinted with melamine.

A mixture of 1.17 g acetonitrile, 0.32 g methacrylic acid, 0.36 g trimethylolpropane trimethacrylate (TRIM), 0.36 g ethylene glycol dimethacrylate (EGDMA), 0.087 g diethyldithiocarbamic acid benzyl ester (living initiator) and 0.02 g pentaerythritol tetrakis(3-mercaptopropionate) (chain transfer agent) was purged with nitrogen and polymerised under UV radiation (UVAPRINT 100 CVI UV source with 0.163 W/cm$^2$ intensity, Dr. Hönle) for 3 min inside a glass column (70×4 mm) packed with glass beads (9–13 μm diameter) derivatised with melamine. Blank (control) particles were synthesized the same way but the column was packed with bare glass beads of the same size. After polymerization the column was washed with 1 ml acetonitrile to elute nanoparticles and unreacted monomers. The resultant soluble imprinted nanoparticles had an average diameter of 60 nm as calculated by dynamic light scattering on a Nanosizer (Malvern Instruments). The size distributions for 3 different runs are shown in FIG. 3.

Example 2

Affinity Separation of Synthesized Polymer a) Preparation of Affinity Adsorbent—Immobilization of Template Glass beads were activated by boiling in 4M NaOH during 10 min, washed with deionised water and acetone then dried at 80° C. for 2 hours. the beads were then incubated in toluene with 2% v/v (3-aminopropyl)trimethoxysilane for 3 hours, washed with acetone and placed in PBS, pH 7.2 with 7% v/v glutaraldehyde for 30 min and afterwards washed with water. The template (melamine) was then immobilized on the surface of the beads by incubation in a solution of PBS pH 7.2 with N-Methyl-2-pyrrolidone (10% v/v) and 0.1 g/ml melamine during 4 hours. The melamine coated particles were used for the synthesis of imprinted nanoparticles and for affinity chromatography.

b) Affinity Chromatography

Figure 1:
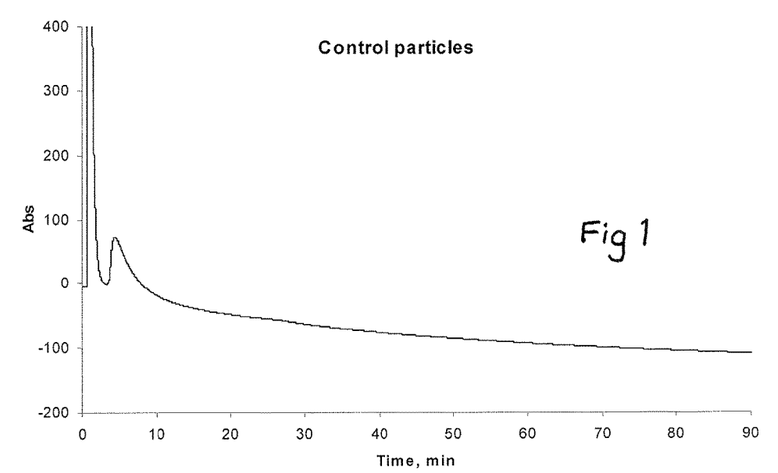
FIG. 1 depicts a chromatogram of blank (control) particles injected on an HPLC column packed with particles coated with immobilized template.
Figure 2:
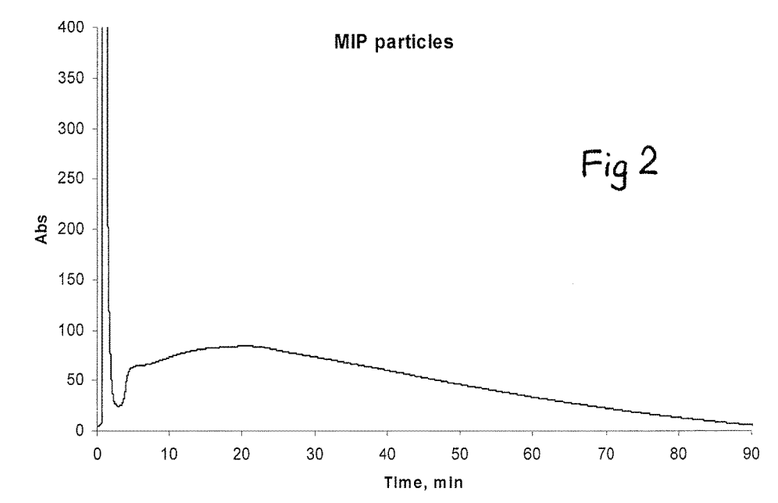
FIG. 2 depicts a chromatogram of MIP particles injected on an HPLC column packed with particles coated with immobilized template.

The sample eluted from the glass column in Example 1 was filtered with a PTFE syringe filter with 0.22 μm pore size in order to remove any large polymer aggregates. To remove unreacted monomers the filtrate was then placed on a centrifuge filter cartridge with a cut-off of 10 000 Da and centrifuged at 3000 g for 4 hours. The particles were then resuspended in acetonitrile and tested on HPLC with a column (100×4.6 mm) packed with the affinity adsorbent prepared as described above (Example 2a) using an Agilent 1100 series HPLC. The injection volume was 40 μl, the mobile phase used was acetonitrile at 1 ml/min and detection was performed at 210 nm. In order to avoid the use of acids to aid elution, analysis was performed at 80° C. Both MIP and control polymers were prepared in the same way. The chromatograms for both blank and imprinted particles on the affinity phase are depicted below in FIGS. 1 and 2.

Example 3

Preparation of Nanoparticles for Melamine

Glass beads (75 μm in diameter) were activated by boiling in 4 M NaOH for 10 minutes, then washed thoroughly with double-distilled water and acetone and dried at 80° C. for 2 hours. The beads were then incubated in 2% v/v solution of 3-aminopropyltrimethyloxysilane (APTMS) in toluene overnight, washed with acetone and incubated in 25 ml of a 5% v/v glutaraldehyde (GA) solution in PBS buffer pH 7.2 for 1 hour, and rinsed with double-distilled water. The template was immobilized by incubating the beads in 0.01 g/ml solution of melamine in PBS pH 7.2 with N-methyl-2-pyrrolidone (NMP) (10% v/v) for 4 hours. The excess of physically adsorbed melamine was removed by washing with double-distilled water and methanol. Derivatised glass beads were dried under vacuum and packed in a quartz column (6.4 mm o.d. with 1.5 mm wall, 150 mm length). 0.32 g methacrylic acid (MAA), 0.36 g trimethylolpropane trimethacrylate (TRIM), 0.36 g ethylene glycol dimethacrylate (EGDMA), 0.087 g N,N'-diethyldithiocarbamic acid benzyl ester and 0.02 g pentaerythritol tetrakis(3-mercaptopropionate) (CTA) were mixed in 1.17 g acetonitrile (ACN) and purged with $N_2$ for 2 minutes. Then 500 μl were injected into the column packed with the affinity media, and polymerised under UV radiation at 366 nm (HB 171/A lamp with, 4×15 W power, PHILIPS) for 2 minutes. After polymerization the column was connected to the HPLC system (Agilent 1100 Series HPLC). The elution was performed at a flow rate of 1 ml/min, with UV detection at 220 nm. For the first 90 minutes ACN was used as mobile phase while the column was kept in an ice bath at 0° C. Then for 45 minutes the mobile phase was switched to ACN with formic acid (10 mM) and the temperature was raised to 25° C. Finally, for 35 minutes the elution of the high affinity fractions of nanoparticles was performed at 60° C. The blank nanoparticles were prepared as described above but made using non-derivatised glass beads. The size of synthesized nanoparticles in different fractions varied from 120 to 460 nm as calculated by dynamic light scattering on a Nanosizer (Malvern Instruments).

Example 4

Preparation of Nanoparticles for Peptide

Glass beads (75 μm diameter) were boiled in 4M NaOH for 10 minutes, washed with double-distilled water and acetone and dried at 80° C. for 2 hours. The beads were then incubated in 2% v/v solution of 3-aminopropyltrimethyloxysilane (APTMS) in toluene overnight, then washed with acetone and incubated in 25 ml of a 7% v/v glutaraldehyde (GA) solution in PBS pH 7.2 for 1 hour, rinsed with double-distilled water and incubated in 0.05 mg/ml solution of peptide (TATTSVLG-NH$_2$) in PBS pH 7.2 for 4 hours. The derivatised beads were washed with double-distilled water and used for the preparation of MIP nanoparticles. 19.5 mg N-isopropylacrylamide (NIPAm), 1 mg N,N'-methylenebisacrylamide (BIS), 16.5 mg N-tert-butylacrylamide (TBAm) and 1.11 μl acrylic acid (AAc) were dissolved in 50 ml H$_2$O, containing 10 mg sodium dodecyl sulphate (SDS). The solution was sonicated for 10 minutes and purged with N$_2$ for 30 minutes. 10 ml of this solution were put in a 20 ml screw cap vial containing 4 g of derivatised glass beads. The polymerization was initiated by adding 100 μl of 60 mg/ml ammonium persulphate (APS) and 3 μl of N,N,N',N'-tetramethylethylenediamine (TEMED) and carried out at room temperature for 22 hours. The bottle containing the MIP product and the affinity media was kept in ice at 0° C. for 10 minutes, and then poured into SPE cartridges to separate the glass beads with attached nanoparticles from the other components. Five washing steps, each with 10 ml of cold double-distilled water, were performed to remove material with low or no affinity. The elution of the high affinity fractions of nanoparticles was performed with PBS pH 7.2 at 60° C. The blank nanoparticles were prepared as described above but made using non-derivatised glass beads. The size of synthesized nanoparticles in different fractions varied from 30 to 130 nm as calculated by dynamic light scattering on a Nanosizer (Malvern Instruments).

Analysis of the Affinity of Synthesized Nanoparticles

Au-coated (SIA Kit Au) chips were cleaned by immersing them in Piranha solution ($H_2SO_4/H_2O_2$, 3:1 v/v) for 5 minutes. Then they were thoroughly rinsed with double-distilled water and ethanol. The immobilisation of thiolated derivative of the peptide template with a glycine spacer (CGGGGTATTSVLG-$NH_2$) and a thiolated reference peptide (CQLPELKQKSS-$NH_2$) was performed and recorded on-line using Biacore 3000 SPR by injecting 100 µl of a 0.1 mg/ml peptide solution in PBS pH 7.4 on a cleaned gold chip with a flow rate of 15 µl/min at 25° C. 100 µl of nanoparticles diluted at 1:10, 1:20, 1:40, 1:60, 1:80 and 1:100 in PBS pH 7.4 were injected (flow rate: 15 µl/min), and the sensor response analysed for 2 minutes using Biacore software. An apparent dissociation constant $K_D$=2.5 pM was obtained for the interaction between the MIP nanoparticles and the template peptide (CGGGGTATTSVLG-$NH_2$). An apparent dissociation constant recorded for reference peptide (CQLPELKQKSS-$NH_2$) was $K_D$=3.3 nM demonstrating that the MIP nanoparticles are about 1000-fold more specific for the template peptide.

Example 5

Preparation of Nanoparticles for Vancomycin

Glass beads (75 µm diameter) were boiled in 4M NaOH for 10 minutes, washed with double-distilled water and acetone and dried at 80° C. for 2 hours. The beads were then incubated in 2% v/v solution of (3-aminopropyl)trimethoxysilane overnight, washed with acetone and placed in PBS buffer pH 7.2 with 7% v/v glutaraldehyde for 1 hour, rinsed with double-distilled water and incubated with 0.5 mg/ml vancomycin HCl in PBS pH 7.2 for 4 hours. The derivatised beads were washed with double-distilled water and used for the preparation of MIP nanoparticles. 19.5 mg N-isopropylacrylamide (NIPAm), 1 mg N,N'-methylenebisacrylamide (BIS), 16.5 mg N-tert-butylacrylamide (TBAm) and 1.11 µl acrylic acid (AAc) were dissolved in 50 ml $H_2O$, containing 10 mg sodium dodecyl sulphate (SDS). The solution was sonicated for 10 minutes and purged with $N_2$ for 30 minutes. 50 ml of this solution were put in a 100 ml screw cap vial containing 20 g of derivatised glass beads. The polymerization was initiated by adding 500 µl of mg/ml ammonium persulphate (APS) and 3 µl of N,N,N',N'-tetramethylethylenediamine (TEMED) and carried out at room temperature for 22 hours. The bottle containing the MIP product and the affinity media was kept in ice at 0° C. for 10 minutes, and then poured into SPE cartridges to separate the glass beads with attached nanoparticles from the other components. Five washing steps, each with 20 ml of cold double-distilled water, have been performed to remove the material with low or no affinity. Then the high-affinity nanoparticles were detached from the affinity media by passing 5 fractions of 20 ml of PBS pH 7.2 at 60° C. Non-imprinted nanoparticles have been prepared in the same way but using the glass beads derivatised with chlorotrimethylsilane. The resultant soluble imprinted nanoparticles had an average diameter of 228 nm, as calculated by dynamic light scattering (DLS) using Zetasizer Nano (Nano-S) from Malvern Instruments Ltd (Malvern, UK).

Analysis of the Affinity of Synthesized Nanoparticles

Au-coated (SIA Kit Au) chips purchased from Biacore were cleaned by immersing them in Piranha solution ($H_2SO_4/H_2O_2$, 3:1 v/v) for 5 minutes. Then they were thoroughly rinsed with double-distilled water and ethanol and incubated in 0.2 mg/ml solution of 4-aminothiophenol in ethanol for 24 hours at 4° C. After this the chips were rinsed with double-distilled water and incubated in 2.5 ml of a 7% v/v solution of GA in PBS pH 7.2 at room temperature for 1 hour. Chips were further rinsed with double-distilled water and incubated in a 1.2 mg/ml solution of vancomycin in PBS pH 7.2 at room temperature for 24 hours and docked into Biacore 3000. 100 µl of nanoparticles and nanoparticles diluted at 1:10, 1:100, 1:1000, 1:10000 in PBS pH 7.4 were injected (flow rate 15 µl/min) at 30° C. The sensor response was analysed using Biacore software. An apparent dissociation constant $K_D$ for vancomycin for MIP nanoparticles was 0.9 nM.

The invention claimed is:

1. A process for the preparation of a solution or colloidal suspension of molecularly imprinted polymer ("MIP") particles comprising the steps of:
    (a) providing a carrier substance having a template material immobilized on it so the template is exposed at the carrier substance surface;
    (b) providing a polymerizable composition in contact with said template;
    (c) effecting controlled polymerization of said polymerizable composition in contact with said template by using a method selected from radical polymerization, optionally controlled living radical polymerization (LRP); living anionic polymerization; living cationic polymerization; and controlled polycondensation; iniferter-mediated polymerization, nitroxide-mediated polymerization (NMP), atom-transfer radical polymerization (ATRP) and reversible addition-fragmentation chain-transfer polymerization (RAFT), said polymerization being terminated when MIP particles of less than 1 micrometer have been formed; and
    (d) separating said MIP particles from said template by washing and/or eluting thereby forming said solution or colloidal suspension, wherein said carrier substance and said immobilized template can be reused in additional controlled polymerizations of the type set forth in step (c) above.

2. A process according to claim 1 in which said carrier substance is in the form of beads, the surface of waveguides, fibers, optical fibers, membranes or capillaries.

3. A process according to claim 1 in which said carrier substance is a polymer resin, a polysaccharide, a glass or a metal surface.

4. A process according to claim 1 where said polymerizable composition contains one or more monomers selected from vinyl monomers, allyl monomers, acetylenes, acrylates, methacrylates, acrylamides, methacrylamides, chloroacrylates, itaconates, trifluoromethylacrylates, derivatives of amino acids, nucleosides, nucleotides, and carbohydrates.

5. A process according to claim 4 wherein said polymerizable composition also contains at least one cross-linker selected from ethylene glycol dimethacrylate, trimethylolpropane trimethacrylate, divinylbenzene, methylene bisacrylamide, ethylene bisacrylamide and N,N'-bisacrylolylpiperazine.

6. A process according to claim 1 wherein, after step (c), a wash step is employed, whereby the synthesized MIP particles are washed, followed by separation of the synthesized particles from the template and the collection of said synthesized particles.

7. A process according to claim 5 wherein in step (c), polymerization is initiated by heating, UV or visible light irradiation, microwave irradiation, electropolymerization, oxidation or adding catalyst.

8. A process according to claim 1 wherein polymerization is terminated when MIP particles of less than 460 nm have been formed.

9. A process according to claim 1 wherein polymerization is terminated when MIP particles of less than 300 nm have been formed.

10. A process for the preparation of a solution or colloidal suspension of molecularly imprinted polymer ("MIP") particles comprising the steps of:
   (a) providing a carrier substance having a template material immobilized on it so the template is exposed at the carrier substance surface;
   (b) providing a polymerizable composition in contact with said template, wherein said polymerizable composition contains one or more monomers selected from vinyl monomers, allyl monomers, acetylenes, acrylates, methacrylates, acrylamides, methacrylamides, chloroacrylates, itaconates, trifluoromethylacrylates, derivatives of amino acids, nucleosides, nucleotides, and carbohydrates, and also contains at least one cross-linker selected from ethylene glycol dimethacrylate, trimethylolpropane trimethacrylate, divinylbenzene, methylene bisacrylamide, ethylene bisacrylamide, and N,N'- bisacryloylpiperazine;
   (c) effecting controlled polymerization of said polymerizable composition in contact with said template by using a method selected from radical polymerization, optionally controlled living radical polymerization (LRP); living anionic polymerization; living cationic polymerization; and controlled polycondensation; iniferter-mediated polymerization, nitroxide-mediated polymerization (NMP), atom-transfer radical polymerization (RAFT), said polymerization being initiated by heating, UV or visible light irradiation, microwave irradiation, electropolymerization, oxidation, or adding catalyst and being terminated when MIP particles of less than 460 nm have been formed;
   (d) washing said MIP particles; and
   (e) separating said MIP particles from said template surface by means of heating, changing solution pH, changing ionic strength, or through the addition of urea, guanidine, or a substance which interacts with the template more strongly than does the MIP thereby forming said solution or colloidal suspension, wherein said carrier substance and said immobilized template can be reused in additional controlled polymerizations of the type set forth in step (c) above.

11. A process according to claim 10 wherein said carrier substance is in the form of beads, the surface of waveguides, fibers, optical fibers, membranes or capillaries.

12. A process according to claim 10 in which said carrier substance is a polymer resin, a polysaccharide, a glass or a metal surface.

* * * * *